United States Patent
Pflaum et al.

(10) Patent No.: US 6,416,219 B1
(45) Date of Patent: Jul. 9, 2002

(54) TREATMENT-DIAGNOSTIC APPARATUS HAVING A POSITIONING DEVICE FOR A PATIENT

(75) Inventors: Michael Pflaum, Adelsdorf; Reinhard Zitzmann, Effeltrich, both of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/564,460

(22) Filed: May 3, 2000

(30) Foreign Application Priority Data

May 3, 1999 (DE) .......................... 199 20 008

(51) Int. Cl.⁷ ............................... H05G 1/02
(52) U.S. Cl. ...................... 378/209; 378/195; 378/196; 378/208
(58) Field of Search ................ 378/195, 196, 378/208, 206, 209

(56) References Cited

U.S. PATENT DOCUMENTS

| | | | | |
|---|---|---|---|---|
| 3,086,115 A | * | 4/1963 | Sutherland | ...................... 108/8 |
| 3,868,103 A | * | 2/1975 | Pageot et al. | .................. 5/614 |
| 4,287,422 A | * | 9/1981 | Kuphal et al. | ............... 378/209 |
| 4,979,202 A | * | 12/1990 | Siczek et al. | ............... 378/198 |
| 5,013,018 A | * | 5/1991 | Siczek et al. | .................. 5/601 |
| 5,014,292 A | * | 5/1991 | Siczek et al. | ............... 378/196 |
| 5,273,043 A | * | 12/1993 | Ruike | .......................... 600/436 |
| 5,410,584 A | * | 4/1995 | Schaefer et al. | ............ 378/196 |
| 5,572,568 A | * | 11/1996 | Kanemitsu | .................. 378/206 |
| 5,822,814 A | * | 10/1998 | Van der Ende | ................ 5/601 |
| 5,930,328 A | * | 7/1999 | Nakamura et al. | ............ 378/91 |
| 6,027,247 A | * | 2/2000 | Tachi et al. | .................. 378/196 |
| 6,203,196 B1 | * | 3/2001 | Meyer et al. | ................ 378/197 |
| 6,246,239 B1 | * | 6/2001 | Krogmann et al. | ......... 324/318 |
| 6,309,102 B1 | * | 10/2001 | Stenfors | ..................... 378/197 |

FOREIGN PATENT DOCUMENTS

DE      OS 197 36 884      3/1999

* cited by examiner

Primary Examiner—Robert H. Kim
Assistant Examiner—Allen C Ho
(74) Attorney, Agent, or Firm—Schiff Hardin & Waite

(57) ABSTRACT

A treatment-diagnostic apparatus has a positioning device with a positioning plate for the treatment and/or examination subject that is adjustable at a base and is transparent for radiation in at least one region. The positioning plate, with reference to the base, is mounted so as to be adjustable at least along its longitudinal axis and is mounted at the base so as to be adjustable in height, as well as around three spatial axes x, y, z. Due to the versatile adjustability, such an apparatus meets the demands for an angiographic diagnostic and/or therapy as well as for surgical procedures.

11 Claims, 7 Drawing Sheets

TREATMENT-DIAGNOSTIC APPARATUS HAVING A POSITIONING DEVICE FOR A PATIENT

BACKGROUND OF THE INVENTION

1. Field of the Invention

The present invention is directed to an apparatus for treatment or diagnosis of a subject, of the type having a positioning device for suitably positioning the subject for a treatment or diagnostic procedure.

2. Description of the Prior Art

Positioning devices for a treatment subject are known that are arranged in an operating room. These positioning devices have a base at which a positioning plate for the treatment subject can be pivoted around its longitudinal axis as well as around its transverse axis and can also be adjusted around a vertical axis. The positioning plate also can be moved along the transverse axis with rotation around the longitudinal axis and can be moved along the longitudinal axis with rotation around the transverse axis.

Positioning devices for an examination subject are known for angiographic examinations that have a positioning plate seated at a base so as to be movable along its longitudinal and transverse axes as well as adjustable in height. The positioning plate is transparent for radiation in at least one region, so that transirradiation exposures of the examination subject can be produced using an exposure unit composed of a radiation emitter and a radiation detector. To this end, the radiation emitter and the radiation detector can be seated opposite one another at the ends of a C-arm that is mounted at a holder so as to be adjustable along its circumference as well as, for example, to be movable along ceiling or floor rails.

When, following the production of, for example, X-ray exposures, an examination subject is to be treated in an open area, as often occurs in angiographic examinations, then the examination subject must be moved from the angiography system into the operating room and must be positioned on the operating table therein. Angiographic work stations are implemented such that they allow X-ray diagnostic images to be produced as well as x-ray images to monitor treatment with a catheter, however, they are not suited for implementing procedures at the open area because the hygienic measures and the device equipment are not adequate for this purpose.

SUMMARY OF THE INVENTION

It is an object of the present invention to provide a diagnostic/treatment apparatus having a positioning device for a subject, which can be used both for diagnostic procedures and treatment procedures without requiring the subject to be re-positioned.

This object is inventively achieved in a treatment and diagnostic apparatus, particularly for surgical procedures, having a positioning device for a treatment and/or examination subject that has a positioning plate for the subject that is adjustable at a base and is transparent for radiation in at least one region, and wherein the positioning plate is mounted so as to be adjustable at least along its longitudinal axis relative to the base, and is adjustable in height as well as around three spatial axes at the base. Such a treatment-diagnostic apparatus thus enables the adjustment of the positioning plate as required in a surgical procedure as well as—due to the radiation transparency in conjunction with the adjustment possibilities of an angiography work station—a radiation diagnosis, particularly angiographic examinations, without a repositioning of the treatment and/or examination subject being required.

It is advantageous when the positioning plate is adjustable in a direction at least approximately perpendicular to its longitudinal axis in order to improve the treatment and/or examination possibilities on the basis of a corresponding positioning of the treatment and/or examination subject.

It is especially advantageous when the treatment-diagnostic apparatus has an exposure unit composed of a radiation emitter and a radiation detector that can be brought from a standby position, wherein free access to the positioning device is possible, into an exposure position for producing radiation exposures. In the standby position, this exposure unit does not impede the work of the operating team, and in the exposure position radiation exposures can be produced during the operation that yield an especially good image quality when the exposure unit is advantageously allocated to an angiography system.

Proceeding from the standby position, the exposure unit preferably can be brought into the exposure position at the left side as well as at the right side of the positioning plate, so that a radiation exposure can be produced and a treatment or operation can be continued without the exposure unit representing a disturbing factor.

It is also advantageous when a rail for accessories is detachably arranged laterally next to the positioning plate, since accessories, such as supports for the extremities, as well as other supply, monitoring and/or operating devices can be arranged at such a rail.

In order to avoid the penetration of fluids or other articles into the region of the base, it is advantageous when the base is surrounded by laminated cladding.

In specific situations, for instance if the line voltage fails or drops, it is advantageous for at least the electromechanical or hydraulic adjustment devices for effecting a tilt of the positioning plate, in addition to being operable with a line voltage, also to be operable with a voltage supply independent therefrom. Thus, the positioning plate can at least still be brought from a tilted position into a horizontal alignment.

DESCRIPTION OF THE PREFERRED EMBODIMENTS

Figure 1:
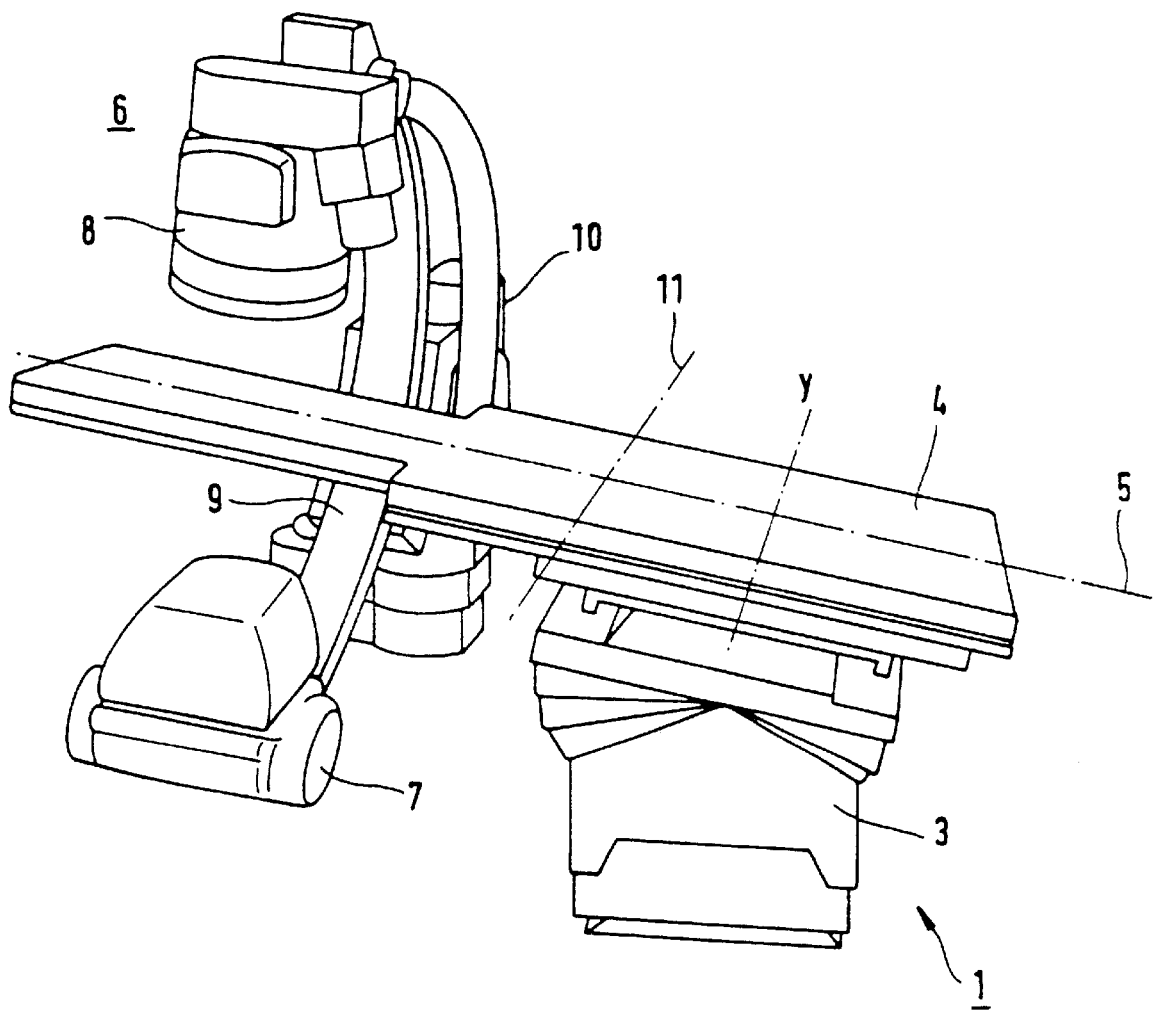
FIG. 1 is a schematic illustration of an treatment-diagnostic apparatus of the invention.
Figure 2:
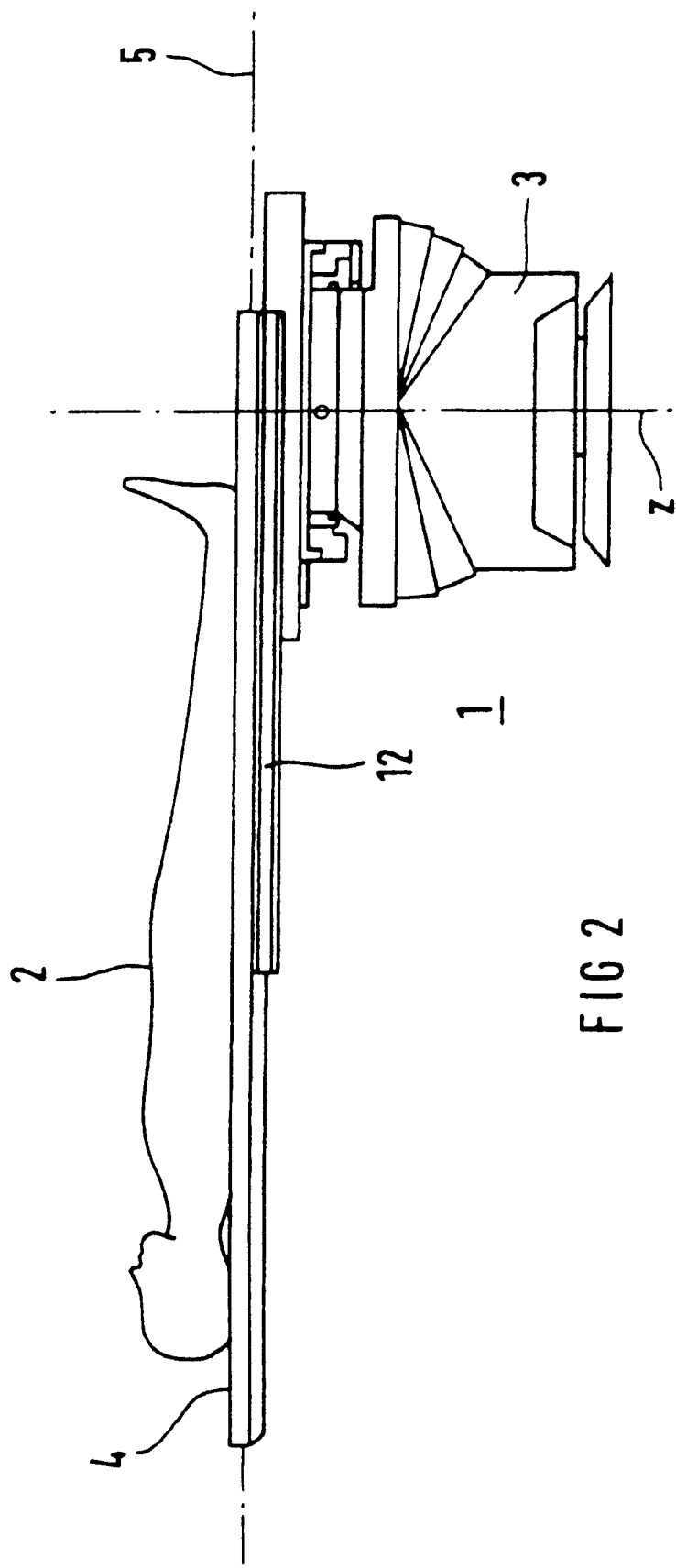
FIG. 2 shows the treatment-diagnostic apparatus of FIG. 1 in a side view.
Figure 3:
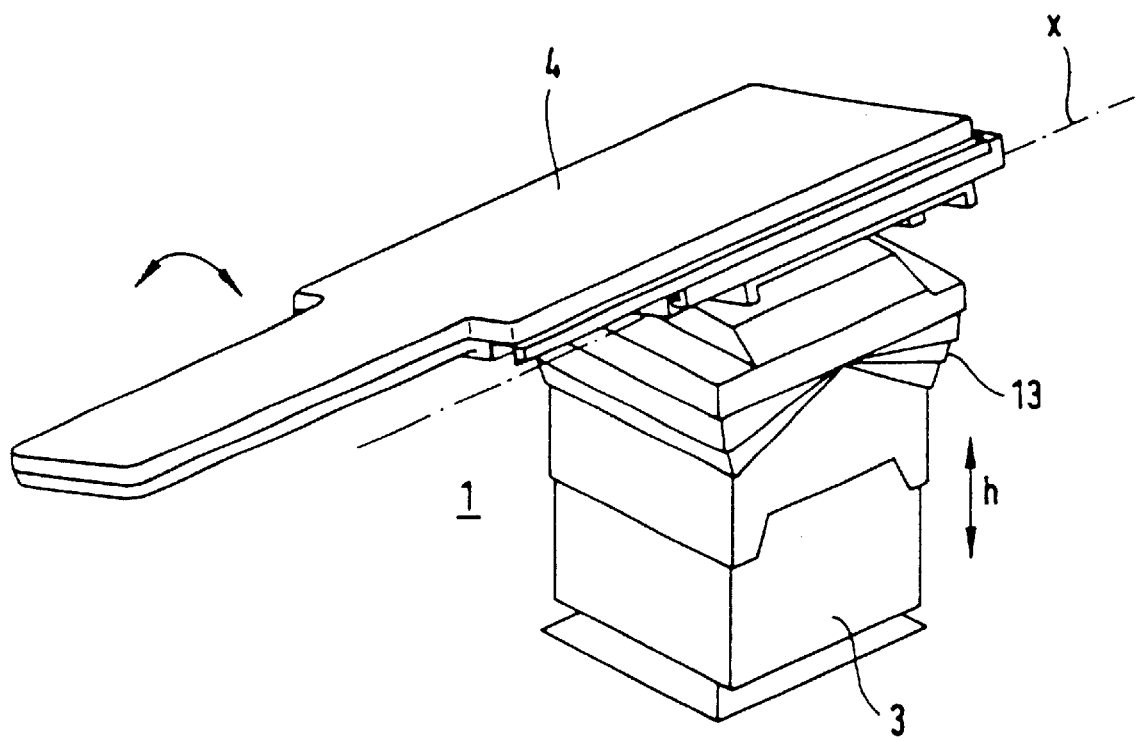
FIG. 3 shows the treatment-diagnostic apparatus of FIG. 2 with a tilted positioning plate.
Figure 4:
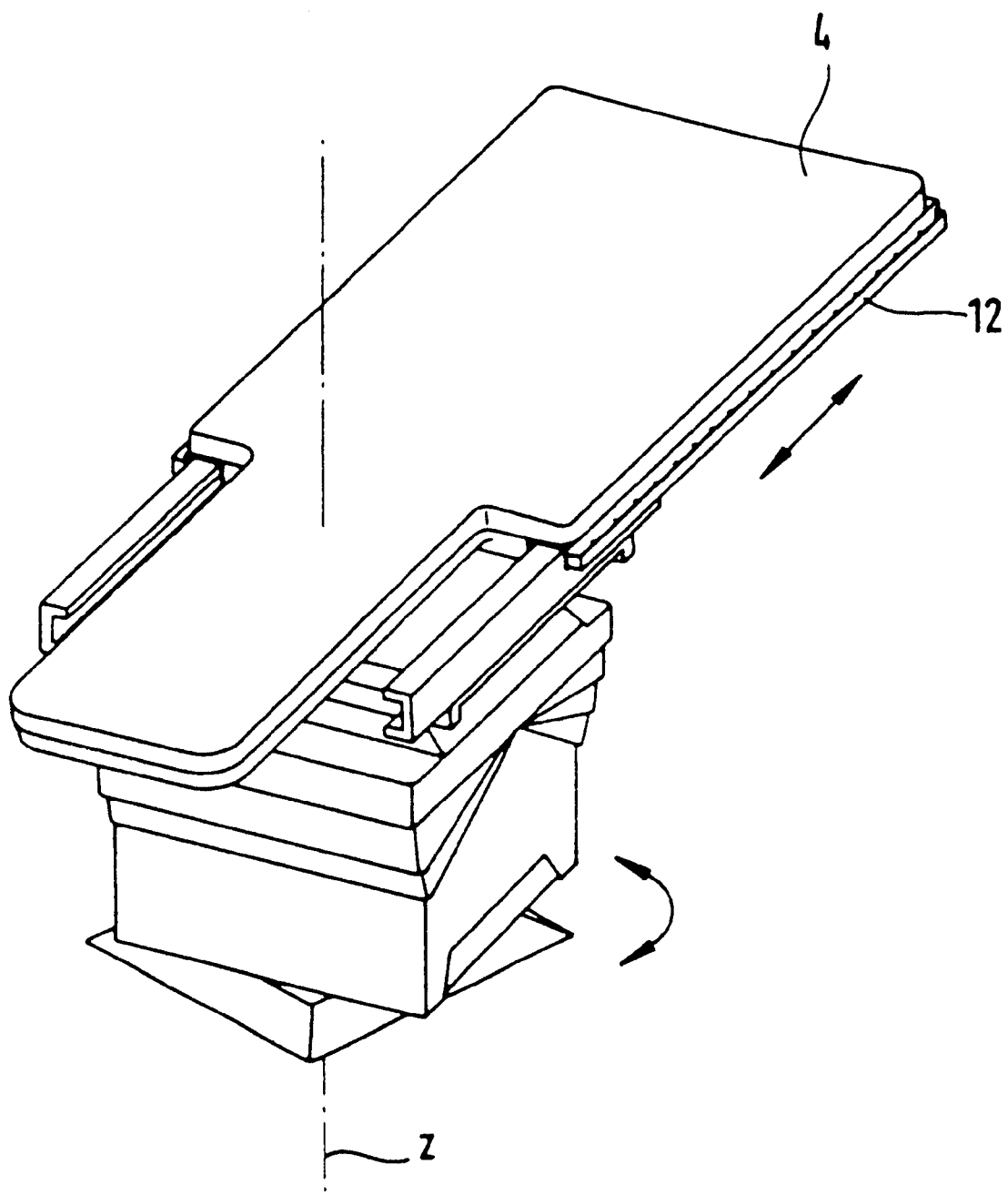
FIG. 4 shows the treatment-diagnostic apparatus of FIG. 2 with the positioning plate adjusted around a vertical axis.
Figure 5:
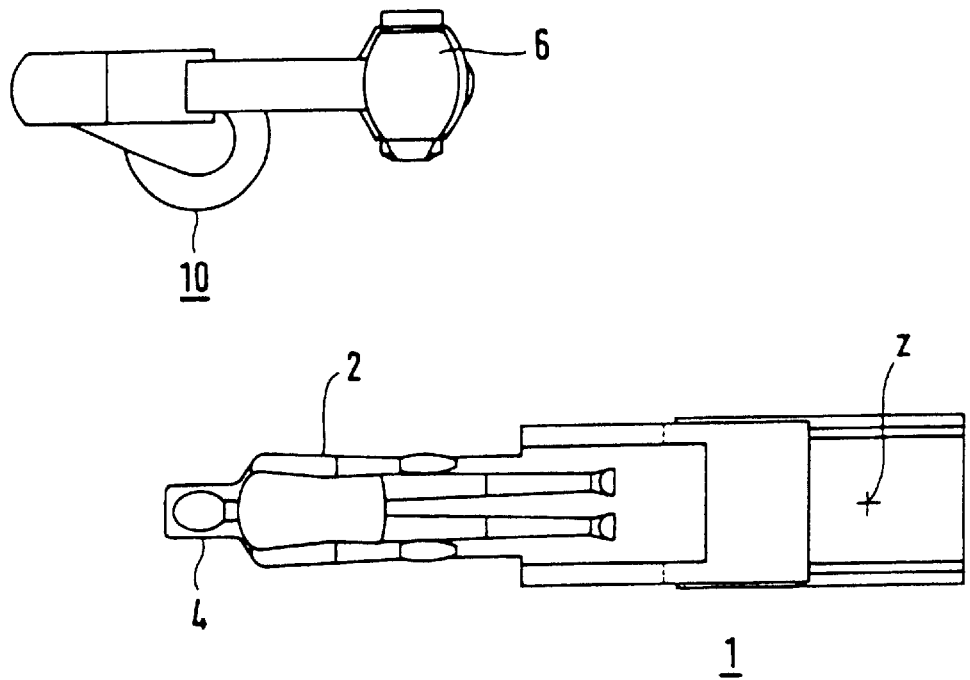
FIG. 5 shows the treatment-diagnostic apparatus of FIG. 1 with the exposure unit in a standby position.
Figure 6:
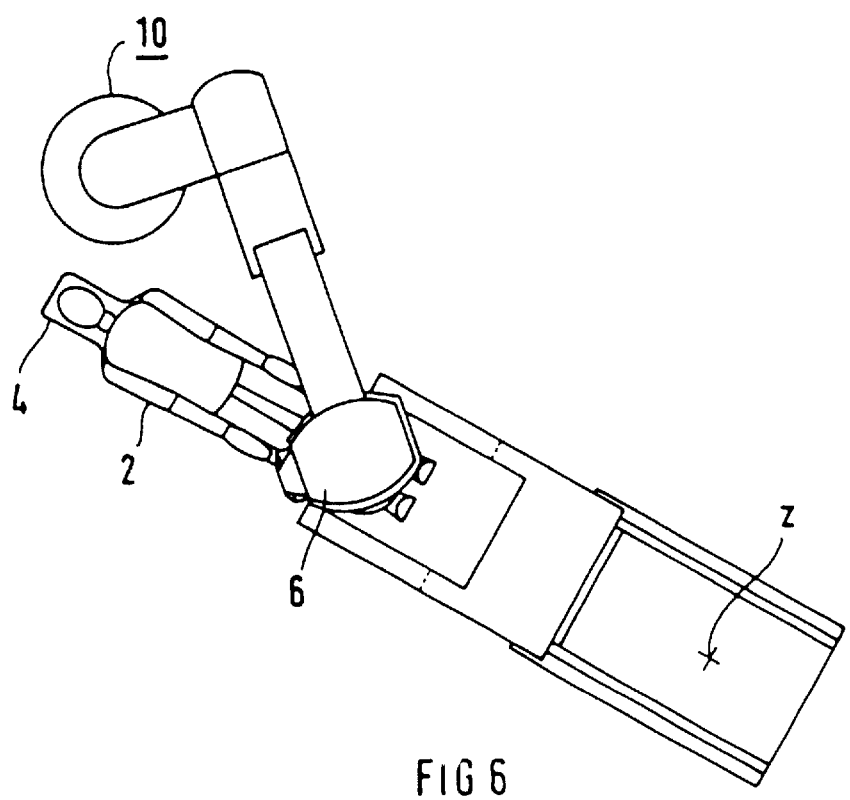
FIG. 6 shows the treatment-diagnostic apparatus of FIG. 1 with the exposure unit in exposure position.
Figure 7:
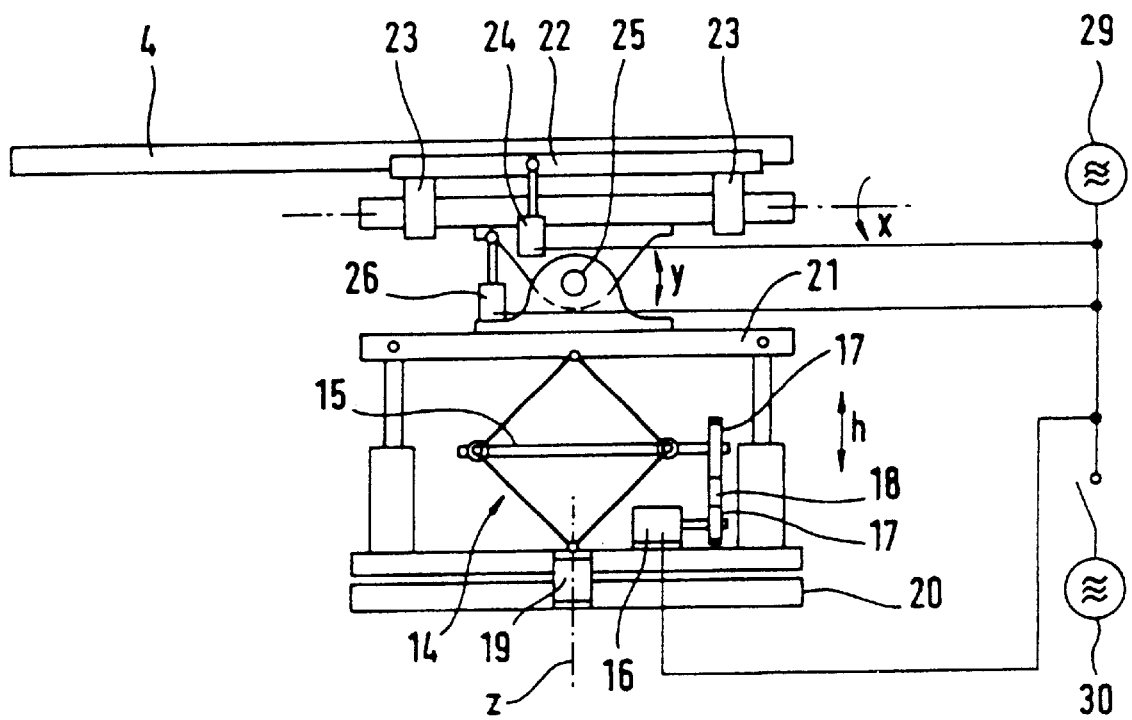
FIG. 7 shows the arrangement of adjustment components of the treatment-diagnostic apparatus according to FIGS. 1 and 2.
Figure 8:
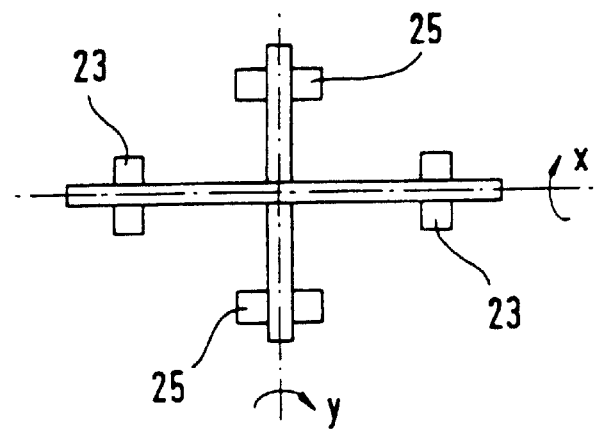
FIG. 8 is a plan view onto the x,y support in the inventive apparatus.

The figures show exemplary embodiments of a treatment-diagnostic apparatus of the invention that has a positioning device 1 for a treatment and/or examination subject 2. A positioning plate 4 that is adjustable at a base 3 and is transparent for radiation in at least one region is provided for the treatment and/or examination subject 2. With reference to the base 3, the positioning plate 4 is mounted so as to be movable at least along its longitudinal axis 5 and is mounted at the base 3 so as to be adjustable in height, as well as around three spatial axes x, y, z. Pivotability of the positioning plate 4, around the y-axis can be seen from FIG. 1, so that the positioning plate 4, or a treatment and/or examination subject 2 arranged thereon, can assume a head or foot position. As also can be seen from FIG. 1, the positioning device 1 has an exposure unit 6 allocated to it, preferably an angiography system composed of a radiation emitter 7 and radiation detector 8 of the treatment-diagnostic apparatus, so that radiological examinations, particularly diagnostic examinations with, for example, X-radiation, can be implemented. In the exemplary embodiment, the radiation emitter 7 and the radiation detector 8—lying opposite one another—are seated at the ends of a C-arm 9 that is adjustably mounted at a floor or ceiling support 10. As can be seen from FIG. 5, the exposure unit 6 is adjusted into a standby position in which free access to the positioning device 1 is possible. As can be seen from FIG. 6, the exposure unit 6 is adjusted into an exposure position in which diagnostic examinations can be implemented at the treatment and/or examination subject 2. In order to enable a left-side hand as well as right-side arrangement of the exposure unit 6 with reference to the positioning plate 4, it can be advantageous—particularly given a stationary support 10—to adjust the positioning plate 4 around the z-axis for this purpose (FIGS. 2, 4, 5, 6). It proceeds from the figures that the positioning plate 4 is mounted so as to be adjustable along its longitudinal axis 5 and, preferably, in the direction of its transverse axis as well. Such a floating support of the positioning plate 4 is known in angiography devices or under-table X-ray diagnostic devices; and therefore need not be discussed in detail. It can be seen from FIG. 2 that a rail 12 for accessories, for example support devices for extremities, treatment, supply and/or operating elements, is provided at the side of and preferably is detachably secured to, the positioning plate 4. A rotation of the positioning plate 4 around the x-axis proceeds from FIG. 3; a laminated cladding 13 of the base 3 can also be seen, which enables a height adjustment of the positioning plate 4 while preventing penetration of fluids and other substances into the interior of the base 3. Electromechanical or hydraulic adjustment devices are provided in order to enable an adjustment of the positioning plate 4, particularly around the x, y and z-axes, as well as a height adjustment h. Exemplary embodiments of such adjustment devices are shown as examples in FIGS. 7, 8 and 9. As can be seen from FIG. 7, the positioning plate 4 is adjustable in terms of its height h via a scissor-type jack 14, to which a motor 16 is engaged via wheels 17 and a belt 18 at the spindle 15 of the scissor-type jack 14 for adjustment. The base 3 is adjustable around the z-axis relative to a bottom plate 20 via a z-pivot bearing. Electromechanical or hydraulic adjustment devices (not shown) can likewise be provided for the adjustment around the z-axis. These adjustment devices should preferably be implemented such that they block an adjustment around the z-axis in a quiescent position, i.e. in which they are not driven. In order to enable rotation of the positioning plate 4 around the x-axis, a further x-pivot bearing 23 as well as an adjustment mechanism, which is implemented as a motor spindle arrangement 24 in the exemplary embodiment, are provided between an upper plate 21 and a support device 22 of the positioning plate 4.

The motor spindle arrangement 24 engages between a y-pivot support 25 and the bearing device 22 for effecting rotation of the positioning plate 4 around the x-axis. For adjusting the positioning plate 4 around the y-axis, the y-pivot bearing 25 is provided between the support device 22 and the upper plate 21. Moreover, a motor spindle arrangement 26 engage, between the x-pivot bearing 23 and the upper plate 21. An exemplary embodiment of an x,y-bearing is shown in a plan view in FIG. 8.

Within the scope of the invention, the function of the x and y pivot bearings can also be assumed by a ball-and-socket joint.

Figure 9:
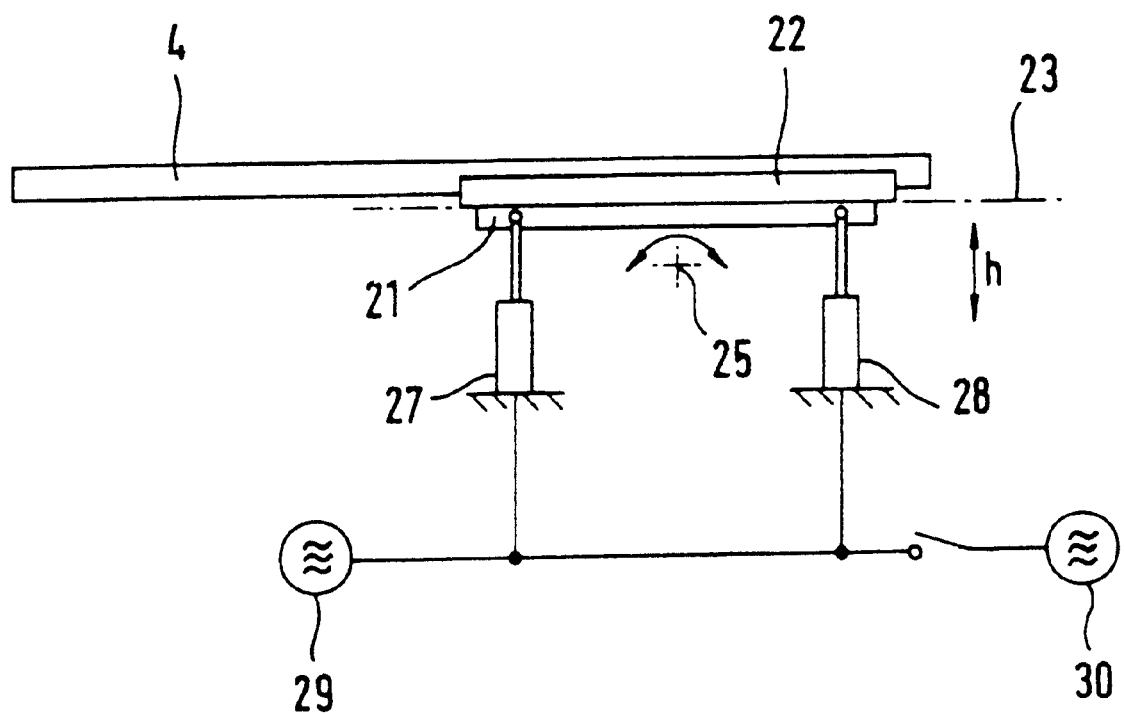
FIG. 9 shows the arrangement of further adjustment components of the treatment-diagnostic apparatus of FIGS. 1 or 2.

A further adjustment component of the treatment-diagnostic apparatus is shown in FIG. 9 wherein first and second lifting mechanisms 27, 28, that can be driven independently of one another or in common, are provided for rotating the positioning plate 4 around the y-axis 25. A rotation of the positioning plate 4 around the y-axis can be effected via an independent drive. To this end, for example, the second lifting mechanism 28 can remain undriven while the first lifting mechanism 27 is driven. The positioning plate 4 thus can be brought into a head or foot position. A common drive of the first and second lifting mechanisms 27, 28 leads to an adjustment of the positioning plate 4 in height h. When the lifting mechanisms 27, 289 are arranged at a first side and, preferably, two further lifting mechanisms are arranged at the opposite side of the support device 22 and when these all engage the support device 22 via, preferably, ball-and-socket joints, then a tilting of the positioning plate 4 around the x-axis 23 can be effected by, for example, a same-sided drive of the lifting mechanisms. A diagonal rotation of the positioning plate is also possible. Alternatively, an x-pivot bearing as well as a motor spindle arrangement also can be provided here for rotating the positioning plate 4 around the x-axis, this motor spindle arrangement engaging between the upper plate4 21 and the bearing device 22. Rotation around the z-axis ensues analogous to the description of FIG. 7.

The adjustment devices for the positioning plate 4 are preferably arranged within the base 3 and are shielded by the aforementioned laminated cladding 13.

In order to maintain the ability to horizontally align the positioning plate 4 even given outage of the line voltage supply, it is advantageous when at least adjustment devices for the adjustment around the x or y axis can be supplied with energy by a voltage supply 30 that is independent of the line voltage supply 29.

Although modifications and changes may be suggested by those skilled in the art, it is the intention of the inventors to embody within the patent warranted hereon all changes and modifications as reasonably and properly come within the scope of their contribution to the art.

We claim as our invention:

1. A treatment-diagnostic apparatus comprising:
  a positioning device adapted for receiving a subject, said positioning device having a positioning plate and a base;
  said positioning plate having a longitudinal axis and having at least one region that is transparent to radiation; and
  a mounting arrangement for mounting said positioning plate directly to a top of said base so that said positioning plate is disposed immediately vertically above and over said top of said base, allowing said positioning plate, relative to said base, to be adjustable at least along said longitudinal axis as well as to be adjustable in height as well as to be always adjustable around three spatial axes.

2. An apparatus as claimed in claim 1 wherein said mounting arrangement allows adjustment of said positioning plate in a direction substantially perpendicular to said longitudinal axis, in addition to adjustment of said height.

3. An apparatus as claimed in claim 1 further comprising a rail for accessories being laterally detachably positionable to said positioning plate and proceeding along at least a portion of a side of said positioning plate.

4. An apparatus as claimed in claim 1 further comprising a laminated cladding covering said base for preventing fluid penetration into said base.

5. An apparatus as claimed in claim 1 wherein said mounting arrangement comprises adjustment devices, selected from the group consisting of electromechanical devices and hydraulic devices, for moving said positioning plate, said adjustment devices including at least one adjustment device for tilting said positioning plate relative to the horizontal, said at least one adjustment device being normally operable from a line voltage, and said apparatus further comprising a voltage supply, independent of said line voltage, for emergency operation of said at least one adjustment device.

6. An apparatus as claimed in claim 5 wherein said adjustment devices are disposed within said base.

7. An apparatus as claimed in claim 1 further comprising an exposure unit, carrying a radiation emitter and a radiation detector, movable from a standby position allowing free access to said positioning device, into an exposure position for producing radiographic exposures of said subject.

8. An apparatus as claimed in claim 7 wherein said exposure unit comprises a C-arm having opposite ends at which said radiation emitter and said radiation detector are respectively mounted.

9. An apparatus as claimed in claim 8 further comprising a mount for said C-arm allowing movement of said C-arm along rails at a ceiling of a room.

10. An apparatus as claimed in claim 8 further comprising a mount for said C-arm allowing movement of said C-arm along rails at a floor of a room.

11. An apparatus as claimed in claim 7 wherein, from said standby position, said exposure unit is selectively movable to an exposure position at a left side of said positioning plate and an exposure position at a right side of said positioning plate.

* * * * *